United States Patent
Goel et al.

(10) Patent No.: US 10,161,641 B2
(45) Date of Patent: *Dec. 25, 2018

(54) REFLECTIVE ULTRAVIOLET LIGHT SHIELD FOR A HVAC UNIT

(71) Applicant: Lennox Industries Inc., Richardson, TX (US)

(72) Inventors: Rakesh Goel, Irving, TX (US); Randall L. Lisbona, Coppell, TX (US)

(73) Assignee: Lennox Industries Inc., Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/657,930

(22) Filed: Jul. 24, 2017

(65) Prior Publication Data

US 2017/0321910 A1    Nov. 9, 2017

Related U.S. Application Data

(63) Continuation of application No. 12/505,664, filed on Jul. 20, 2009, now Pat. No. 9,726,388.

(51) Int. Cl.
| | |
|---|---|
| *F25D 23/00* | (2006.01) |
| *F24F 3/16* | (2006.01) |
| *A61L 9/20* | (2006.01) |
| *F24F 13/22* | (2006.01) |
| *F24F 6/00* | (2006.01) |

(52) U.S. Cl.
CPC .................. *F24F 3/16* (2013.01); *A61L 9/20* (2013.01); *F24F 13/22* (2013.01); *A61L 2209/16* (2013.01); *A61L 2209/212* (2013.01); *F24F 2003/1667* (2013.01); *F24F 2006/006* (2013.01); *Y10T 29/4935* (2015.01)

(58) Field of Classification Search
CPC .. A61L 2209/16; A61L 2209/212; A61L 9/20; F24F 2003/1667; F24F 2006/006; F24F 3/16

See application file for complete search history.

(56) References Cited

U.S. PATENT DOCUMENTS

| | | |
|---|---|---|
| 1,471,024 A | 10/1923 | David |
| 2,798,147 A | 7/1957 | Orsatti |
| 2,837,632 A | 6/1958 | Lipscomb |
| 2,906,104 A | 9/1959 | Schaefer et al. |
| 3,317,107 A | 5/1967 | Williams |

(Continued)

FOREIGN PATENT DOCUMENTS

| | | |
|---|---|---|
| JP | 405103588 A | 4/1993 |
| JP | 410274713 | 10/1998 |

*Primary Examiner* — Filip Zec
(74) *Attorney, Agent, or Firm* — Winstead PC

(57) ABSTRACT

A heating, ventilating and air conditioning (HVAC) unit. The unit comprises a heat exchanger or drain pan located inside a HVAC housing that has one or more access openings and ultraviolet light-sensitive components therein. The unit also comprises a light located inside of the HVAC housing and a light shield located between the heat exchanger or drain pan and the light source. The light source includes a network of open-ended cells, each cell having ultraviolet light reflective walls. The light shield is oriented to direct an ultraviolet light from the light source through the open-ended cells towards the heat exchanger or drain pan and away from the one or more access openings and ultraviolet light-sensitive components.

20 Claims, 5 Drawing Sheets

FIG. 3B

(56) References Cited

U.S. PATENT DOCUMENTS

| | | | |
|---|---|---|---|
| 3,691,261 A | 9/1972 | Cusano et al. | |
| 3,926,556 A | 12/1975 | Boucher | |
| 4,786,812 A | 11/1988 | Humphreys | |
| 5,112,370 A | 5/1992 | Gazzano | |
| 5,235,497 A | 8/1993 | Costa | |
| 5,330,722 A | 7/1994 | Pick et al. | |
| 6,154,311 A | 11/2000 | Simmons, Jr. et al. | |
| 6,238,065 B1 | 5/2001 | Jones | |
| 6,557,356 B2 | 5/2003 | Underwood | |
| 6,679,068 B1 | 1/2004 | Guzorek | |
| 6,972,421 B2 | 12/2005 | Melnychuk et al. | |
| 7,261,435 B2 | 8/2007 | Gould et al. | |
| 7,332,124 B2 | 2/2008 | Trifu et al. | |
| 7,563,004 B2 | 7/2009 | Pickard et al. | |
| 8,011,149 B2 | 9/2011 | Knudsen | |
| 8,242,039 B2 | 8/2012 | Sugawara | |
| 8,350,228 B2 * | 1/2013 | Welker | A61L 9/20 250/435 |
| 2005/0190568 A1 | 9/2005 | Sevack et al. | |
| 2006/0037330 A1 | 2/2006 | Weigl | |
| 2007/0059225 A1 * | 3/2007 | Willette | A61L 9/16 422/186.3 |
| 2010/0108998 A1 | 5/2010 | Verjans et al. | |

* cited by examiner

REFLECTIVE ULTRAVIOLET LIGHT SHIELD FOR A HVAC UNIT

CROSS REFERENCE TO RELATED INFORMATION

This application is a continuation of U.S. patent application Ser. No. 12/505,664, filed Jul. 20, 2009, titled Reflective Ultraviolet Light Shield for a HVAC Unit, now U.S. Pat. No. 9,726,388, the contents of which are hereby incorporated herein in its entirety.

TECHNICAL FIELD

This application is directed, in general, to heating, ventilating and air conditioning units, and more specifically, to heating, ventilating and air conditioning units having an ultraviolet light shield and to methods of manufacturing such units.

BACKGROUND OF THE INVENTION

Water can condense on the heat exchangers (e.g., evaporator fins and cooling coils) or drain pans of heating, ventilating and air conditioning (HVAC) units, thereby providing a favorable environment for microorganisms (e.g., mold, pollen, bacteria etc. . . . ). The presence of such materials can detrimentally affect the quality of air passed through the heat exchanger. In some cases ultraviolet (UV) light is used to degrade or kill the microorganisms. UV light exposure however, can degrade UV-sensitive components in a HVAC unit, thereby shortening the operable lifetime of these components. UV light exposure can also damage human tissue (e.g., the eyes) thereby presenting a potential hazard to individuals servicing HVAC units.

BRIEF SUMMARY OF THE INVENTION

One embodiment of the present disclosure is a heating, ventilating and air conditioning (HVAC) unit. The unit comprises a heat exchanger or drain pan located inside a HVAC housing that has one or more access openings and ultraviolet light-sensitive components therein. The unit also comprises a light located inside of the HVAC housing and a light shield located at least partially between the heat exchanger or drain pan and the light source. The light source includes a network of open-ended cells, each cell having ultraviolet light reflective walls. The light shield is oriented to direct an ultraviolet light from the light source through the open-ended cells towards the heat exchanger or drain pan and away from the one or more access openings and ultraviolet light-sensitive components.

Another embodiment of the present disclosure is a method of manufacturing a HVAC unit. The method comprises providing a HVAC housing having one or more access openings and ultraviolet light-sensitive components. The method further comprises placing a heat exchanger or drain pan inside of the HVAC housing such that the heat exchanger or drain pan are located between paths for conditioned air and return airflow. The method also comprises locating a light source inside of the HVAC housing such that ultraviolet light emitted from the light source can reach the heat exchanger or drain pan. The method further comprises situating the above-described light shield at least partially between the heat exchanger or drain pan and the light source in the HVAC housing.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Reference is now made to the following descriptions taken in conjunction with the accompanying drawings, in which.

DETAILED DESCRIPTION OF THE INVENTION

It was discovered that placing a light shield between a light source and heat exchanger or drain pan facilitates directing UV light emitted from said light source towards the heat exchanger or drain pan and away from access openings or UV-sensitive components inside a HVAC unit. The light shield is designed to minimize the loss of UV light transmitted from the light source to the heat exchanger or drain pan, and at the same time, minimize the amount UV light transmitted from the light source to access openings or plastic UV-sensitive components of the HVAC unit. By minimizing the amount of UV light transmitted from the light source to access openings or UV-sensitive components, potentially harmful human exposure and the degradation of the components can be mitigated.

Figure 1:
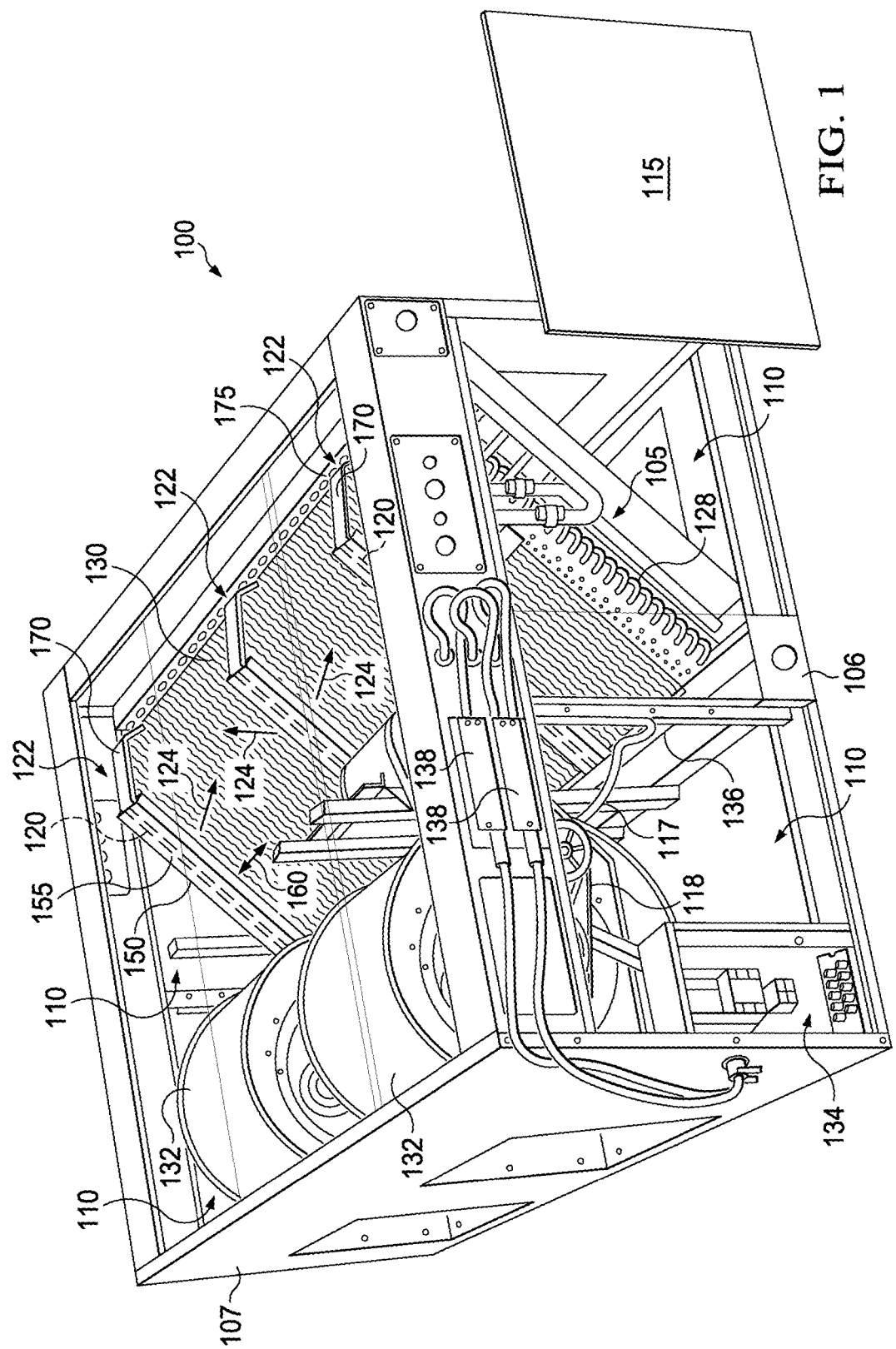
FIG. 1 presents a perspective view of an example embodiment of an HVAC unit of the disclosure.

One embodiment of the present disclosure is a HVAC unit. FIG. 1 presents a perspective view of an example embodiment of an HVAC unit 100 of the disclosure. Some over lying features (e.g., the unit's top and side panel covers) are not shown so as to more clearly depict underlying features.

The unit 100 comprises a heat exchanger 105 or drain pan 106 located inside a HVAC housing 107. As illustrated, both the heat exchanger 105 and drain pan 106 located inside a HVAC housing 107. The housing 107 can have one or more access openings 110. During the unit's normal operation, the access openings 110 are normally covered by access panels 115, but for clarity, are shown with the panels 115 removed in FIG. 1). The HVAC housing 107 also holds UV light sensitive components 117, 118 therein. The unit 100 also comprises a light source 120 located inside of the HVAC housing 107. The unit 100 comprises a light shield 122 which is at least partly located between the heat exchanger 105 or drain pan 106 and the light source 120.

The light source 120 is configured to emit UV light 124 (e.g., light having a peak in intensity at a wavelength in the range of about 200 to 300 nm). Because of its greater efficiency at destroying microbes than other wavelengths, some preferred embodiments of the light source 120 emit C-band UV light 124 (light having a peak in intensity at a wavelength in the range of about 254 to 265 nm). In some embodiments such as shown in FIG. 1, the light source 120 can include, or is, one or more cylindrically-shaped light bulbs.

Those skilled in the art would be familiar with the various components the HVAC unit 100 could include, and the possible embodiments of heat exchanger 105, drain pan 106, housing 107, access openings 110. For instance, the heat exchanger 105 can include assembles of coils 128 and fins 130. The drain pan 106 can be an assembly of metal or plastic sheets. The housing 107 can comprise metal sheets welded together, and configured for mounting inside or outside of a building (e.g., a housing for a roof-top HVAC unit). The access openings 110 can include openings giving access to the heat exchanger 105, drain pan 106, blowers 132, control board 134, or other components such as baffles 136 and ballasts 138 of the unit 100. The UV light-sensitive components can include electrical insulation 117 (e.g. insulation surrounding wires or electronic parts), belts 118 that contain plastics, or other components, such as paper or plastic air filters or plastic coupling or mounting structures (not shown) that are known to be degraded by UV light.

In some preferred embodiments, the light source 120 and light shield 122 cooperate to distribute the UV light 124 at an average intensity of at least about 50 µW/cm2 to a facing surface of the heat exchanger 105 and at an average intensity of about 25 µW/cm2 or less, and more preferably about 15 µW/cm2 or less, to surfaces of the access openings 110 and ultraviolet light-sensitive components 117, 118.

Figure 2:
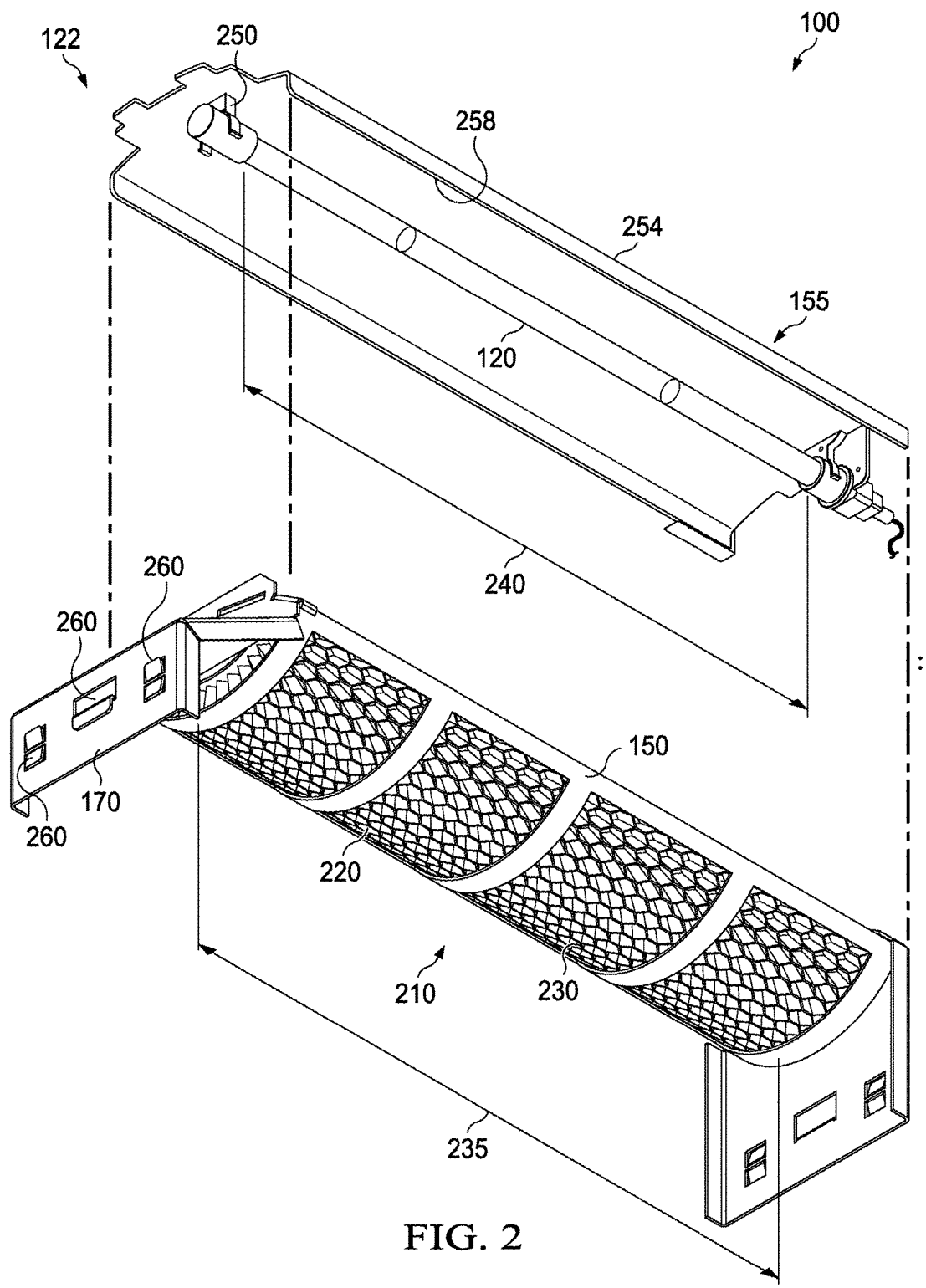
FIG. 2 presents an exploded perspective view of an example embodiment of a light shield of the HVAC unit of the disclosure, such as the light shield of FIG. 1.
Figure 3A:
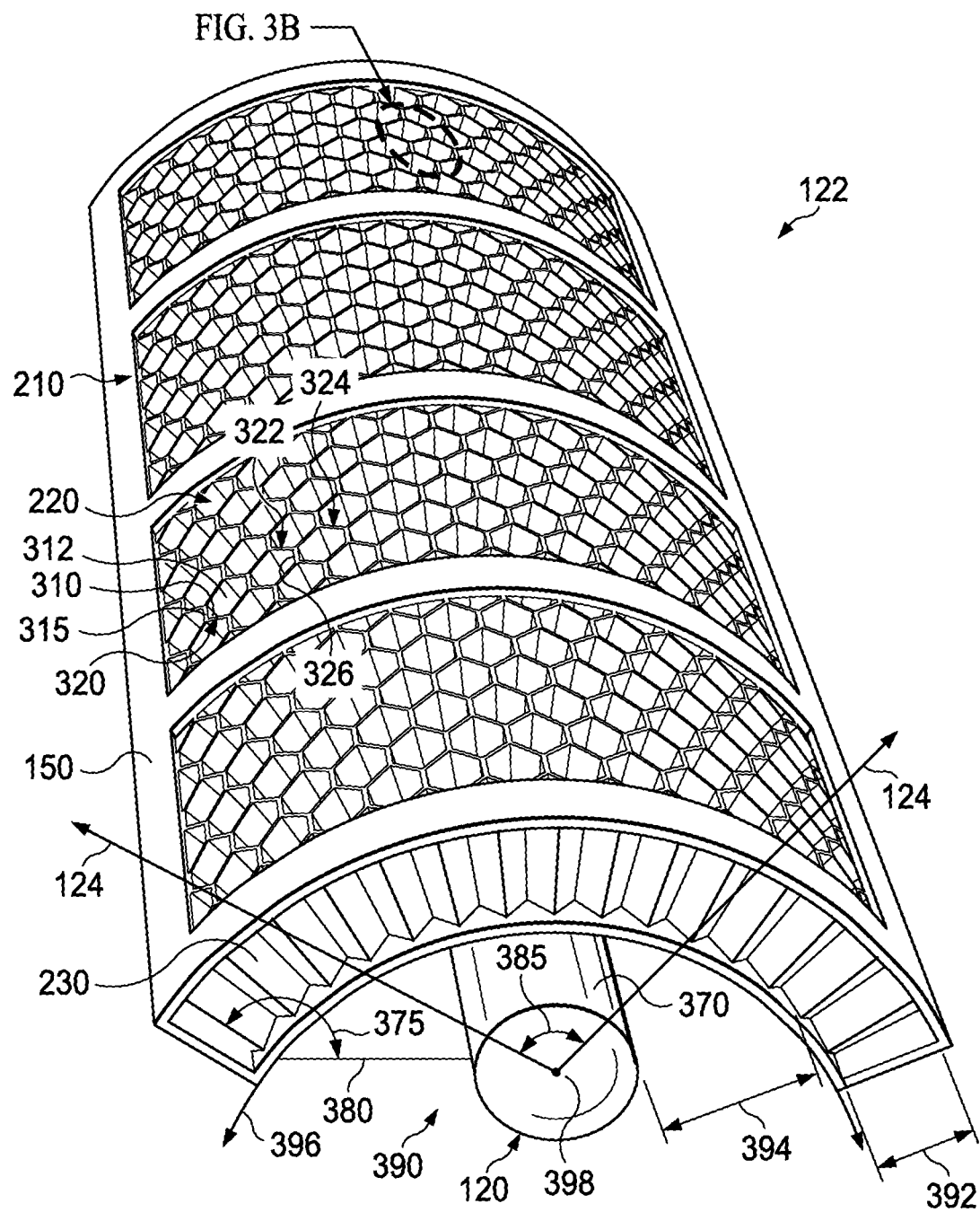
FIG. 3A presents a detailed perspective view of an example embodiment of a light shield of the HVAC unit of the disclosure, such as the light shield of FIG. 1.

FIG. 2 presents an exploded perspective view of an example embodiment of a light shield 122 of the HVAC unit 100 of the disclosure, such as the light shield 122 shown in FIG. 1. FIG. 3A presents detailed perspective views of the example light shield 122 shown in FIG. 2.

The light shield 122 includes a network 210 of open-ended cells 220 having UV light reflective walls 230. The light shield 122 is oriented to direct an UV light 124 (FIG. 1) from the light source 120 through the open-ended cells 220 towards the heat exchanger 105 or drain pan 106 and away from the access openings 110 and UV light-sensitive components 117, 118.

A UV light reflective wall 230 refers to a material that has a reflection coefficient towards UV light of 0.5 or greater. The material can be a layer on the wall 230, or can be the material that the wall 230 is composed of. Examples of suitable materials include metals or metal alloys having a reflection coefficient equal to or greater than about 0.5, such as steel (e.g. galvanized steel), or more preferably, aluminum (having reflection coefficient equal to about 0.7).

In some embodiments, open-ended cells 220 of the network 210 are defined by three or more walls 230. Each pair of adjacent ones of the walls 230 meets to form edges of the cell 220. For instance, the open-ended cells 220 of the network 210 shown in FIG. 3A are defined by four walls 230 that meet to thereby forming a six-walled honeycomb network 210. For instance, two walls 310, 312 that are adjacent to each other meet to form an edge 315 of a cell 320. The edge 315 corresponds to a line segment where the two walls 310, 312 meet. As further illustrated in FIG. 3A, each wall 230 can be shared by at least two of the open-ended cells 220 of the network 210. For instance, a wall 326 of cell 322 is also a wall 326 of an adjacent cell 324.

In some embodiments, it is desirable for each of the open-ended cells to have the same uniform geometric shape. Having a same uniform geometric shape is desirable because it is easier to predict the region of the heat exchanger 105 or drain pan 106 that is covered by the UV light 124 exiting the light shield 122 (FIG. 1). Consequently, the open areas at the ends of the cells will have a geometric shape that is prescribed by the shape of the cells. This is further illustrated in FIG. 3B, which presents a wire-frame perspective view of selected example cells 340, 345 of the light shield 122. For instance, the open areas 350, 352 at the ends 355, 357 the cells 340, 345 can have a hexagonal-honey comb shape. In other embodiments, the open areas 350, 352 could have triangular, diamond, square, pentagonal, heptagonal, octagonal, or other regular geometric shapes well-known to those skilled in the art. In still other embodiments, however, the open areas 350, 352 do have a uniform geometric shape.

Figure 3B:
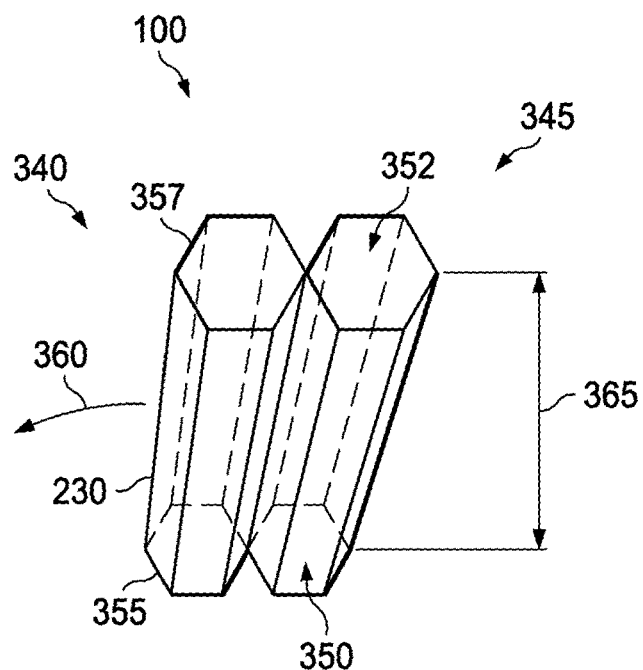
FIG. 3B presents a wire-frame perspective view of selected cells of the light shield shown in FIG. 3A.

As illustrated in FIGS. 3A and 3B, for some embodiments, each of the UV light reflective walls 230 is substantially planar. Excessive curvature in the walls 230 could undesirably decrease the efficient transmission of UV light 124 through the light shield 122 and away from access openings 110 and UV light sensitive components 117, 118. The term substantially planar as used herein is defined as a radius of curvature 360 of each of the walls 230 that is equal to or greater than a length 365 of the walls substantially in the direction that the UV light 124 travels through the cells 220 (FIG. 3B). For instance, if the wall's length 365 equals about 5 cm, the radius of curvature 360 is at least about 5 cm.

In some embodiments, each of the reflective walls is orientated substantially perpendicular to the nearest surface of the light source. Consequently, light emitted from the light source travels in a direction that is parallel to the walls. Such an orientation is conducive to the efficient transmission of UV light 124 through the light shield 122 to the heat exchanger 105 or drain pan 106 and away from access openings 110 and UV light sensitive components 117, 118 (FIG. 1). For example, as illustrated in FIG. 3A, when the light source 120 includes, or is, a cylindrically shaped bulb, the nearest surface 370 of the light source 120 is that curved portion of the bulb that is closest to each of the reflective walls 230. Each of the reflective walls 230 forms an angle 375 with respect to a straight path 380 to the nearest surface 210 that ranges from about −45 to 45 degrees, more preferably equals about 0 degrees.

In some embodiments, such as shown in FIG. 3A, the orientation of the light shield 122 is such that the UV light 124 projects out of the network 210 over an angle 385 that in a range from about 45 to 180 degrees. For instance, in some embodiments, where it is desirable for the UV light 124 to reach only a small area (e.g., just the drain pan, FIG. 1) then the projection angle 385 may be in the range of about 45 to 90 degrees. For instance, in some embodiments, where it is desirable for the UV light 124 to reach a large area (e.g., a non-planar arrange of heat exchangers 105, FIG. 1) then the projection angle 385 may be in the range of about 140 to 180 degrees (e.g., about 150 degrees in some cases).

The network 210 of open-ended cells 220 can have a variety of shapes and dimensions that facilitate the light shield's ability to direct the UV light 120 to the heat exchanger 105 or drain pan 106 and away from access openings 110 and UV light sensitive components 117, 118.

For instance, as illustrated in FIGS. 2 and 3A, the network 210 of open-ended cells 220 can have a cylindrical hemi-annular shape. In some embodiments, the light source 120 is located inside of a concave cavity 390 of semi-cylindrical hemi-annular shaped network 210. Such embodiments help to distribute the UV light 120 uniformly over the heat exchanger 105 or drain pan 106.

For instance, in some embodiments, as shown in FIG. 2, to ensure the desired orientation of the light 124, the semi-cylindrical hemi-annular shaped network 210 has a long axis 235 length that is substantially equal to the length of the long axis 240 of the cylindrically-shaped bulb light source 120 (e.g., same length with ±10 percent). For example, when the bulb 120 has a long axis length 240 of about 61 cm the network's long axis 235 length equals about 61±6 cm. In some embodiments, each bulb's long axis 240 is substantially centrally aligned with, and parallel to, the heat exchanger 105. This can facilitate providing a uniform distribution of UV light 124 to a broad area of the heat exchange 105. In other cases, however, other considerations, such as space limitation inside of the housing, or, the use of a non-planar heat exchanger 105 configurations, can make it desirable to orient the bulb's long axis 240 and light shield 122 non-parallel or non-central to the exchanger 105.

For instance, in some embodiments, as shown in FIG. 3A, the cylindrical hemi-annular shaped network 210 has a radial thickness 392 that ranges from about 1 to 5 cm, and more preferably about 2.5 cm. As illustrated in FIGS. 3A and 3B, the radial thickness 392 can be substantially equal to the length 365 of the cell's walls 230.

In some embodiments, a first open end of each of the cells that is closest to the light source has a smaller open area than an open area of a second open end of the cells. For instance, as shown in FIG. 3B, for a semi-cylindrical hemi-annular shaped network 210, the smaller first open area 350 of the first end 355, can be closest to the light source 120, and, the second larger open area 352 of the second opposite end 357 can be farthest from the light source 120. In some embodiments, the first open area 350 is in a range of about 1 to 10 cm2 and the second open area 352 is about 1.5 to 2.5 times larger than the first open area 350. Having the second open area 352 larger than the first open area 350 can help to distribute the UV light 120 over a larger region of the heat exchanger 105, as compared to when the first and second ends 355, 357 had substantially the same size of open areas.

Figure 4:
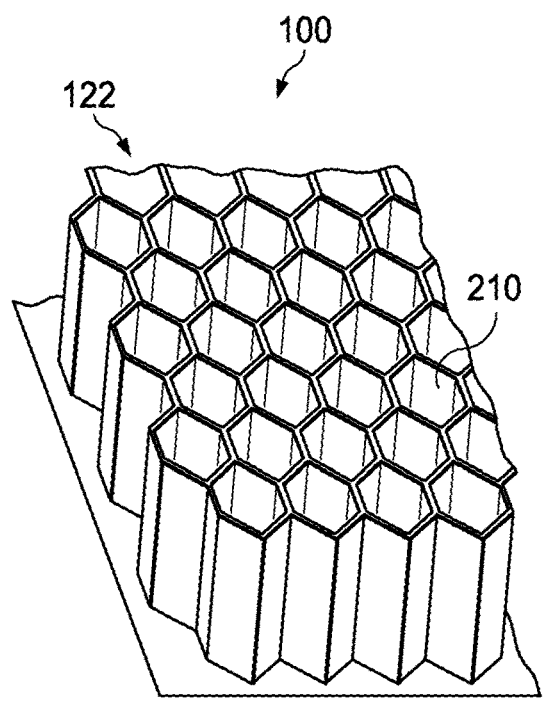
FIG. 4 presents a detailed perspective view of an another example embodiment of a light shield of the HVAC unit of the disclosure, such as the light shield shown in FIG. 1.

In other instances, the network 210 of open-ended cells 220 can have a substantially planar rectangular shape. Such an embodiment is illustrated in FIG. 4, which presents a detailed perspective view of another example embodiment of the light shield 122. A substantially planar rectangular-shaped network 210 may be advantageous in cases instances where the space available in the HVAC housing 107 (FIG. 1) is small. A substantially planar rectangular-shaped network 210 may also have lower manufacturing costs than non-planar shaped networks such as a semi-cylindrical hemi-annular shaped network 210.

In some embodiments, the light shield 122 further includes a frame 150 (FIG. 1) configured to maintain the network's shape. For instance, the light shield 120 shown in FIG. 2 has a frame 150 that helps to maintain the network 210 in a semi-cylindrical hemi-annular shape. For instance, the light shield 120 shown in FIG. 2 has a frame 150 that helps to maintain the network 210 in a planar-rectangular shape. In some cases, FIG. 3A, portions of the frame 150 can also serve to block light 124 passing through certain cells 220 such that the UV light 124 is directed away from certain locations in the housing 107 (e.g., the access openings 110 and UV light-sensitive components 117, 118).

As shown in FIG. 1, in some embodiments, the light shield 122 further includes a cover 155. As shown in FIG. 2 the cover 155 can be configured to hold the light source 120 a fixed distance away from the network 210. The cover 155 can include light mounting brackets 250 that attach the light source 120 to a body 254 of the cover 155. The cover 155 can be shaped to fit tightly over the portion of the network 210 that faces the heat exchanger 105 or drain pan 106, such that the UV light cannot pass out of the light shield 122 other than through the cells 220 of the network 210. The cover 155 can also serve to block the UV light such that it does not illuminate undesirable locations in the housing 107 (e.g., the access openings 110 and UV light-sensitive components 117, 118).

The specific position and distance of the light source relative to the network and heat exchanger or drain pan are additional important variables that affects the intensity and direction of UV light that passes through the cells towards the heat exchanger or drain pan and away from access openings and UV light-sensitive components.

For instance, as shown in FIG. 3A, if the distance 394 separating the opposing surfaces of the network 210 and light source 120 is too large, the size of the light shield 122 may be bigger than desired to fit inside of the housing 107 (FIG. 1). If the distance 394 separating the opposing surfaces of the network 210 and light source 122 is too small, the ability of the cells 220 to direct the UV light 124 towards (the heater exchange 105) and away (e.g., the access openings 110 and UV light-sensitive components 117, 118) from the desired locations in the housing 107 may be hampered. In some embodiments, the opposing surfaces of the network 210 and light source 122, e.g., such as depicted in FIG. 2, are separated by a distance 394 that ranges from about 1 to 10 cm.

For instance, in some embodiments, such as when the network 210 has a cylindrical hemi-annular shape, the network 210 can at least partial circumscribe the long axis 122 of a light source 120 configured as a cylindrical bulb. This orientation helps to direct greater amounts of the light 124 towards and away from the desired directions in the unit 100. For example, the network 210 can circumscribe an about 45 or greater angle 396 around the bulb's long axis 122. In some cases, the bulb's long axis 122 is preferably located substantially at a radial center 398 of the network's hemi-annulus (e.g., the network's radial center, if the hemi-annular shape were extended to a full annulus).

For instance, if the distance 160 (FIG. 1) separating the outer surface of the network 210 and the heat exchanger 105 or drain pan 106 is too large, then the germicidal effectiveness of the light 124 emitted from the light source 120 may not be effective. If the distance 160 is too small then the only a small portion of the heat exchange may be illuminated by any one light source, thereby necessitating the inclusion of more light sources 120 and light shields 122 inside the housing 107. In some embodiments, the outer surface of the network 210 is separated from the heat exchanger 105 or drain pan 106 by a distance 160 that ranges from about 10 to 30 cm (FIG. 1).

In some embodiments, as shown in FIG. 2, an interior surface 258 of the cover 155 is UV light reflective. Having a UV light-reflective interior surface 258 facilitates the efficient transmission of UV light emitted by the light source 120 through the cells 220 of the network 210. For instance, instead of being substantially absorbed by the interior surface 258, the UV light can be reflected off of the cover's surface 258 towards the network 210. The interior surface 258 can comprise same type of materials as the UV light reflective walls 230. For instance, the interior surface 258 preferably has a reflection coefficient for UV light of about 0.5 or greater. For instance, in some cases, the cover 155 is made, or has an interior material layer, of aluminum or steel.

As shown in FIG. 1, in some embodiments, the light shield 122 further includes a housing mounting bracket 170 configured to connect the light shield 122 to the HVAC housing 107 so as to provide the desired orientation of the light shield 122 with respect to the heater exchange 105. For instance, the light shield 122 can mounted inside of the housing 107 by connecting the brackets 170 to fixtures 175 of the housing 107, e.g., via a snap lock mechanism 260 (FIG. 2).

In some embodiments, such as shown in FIG. 2, the light shield 122 has one or more housing mounting brackets 170 attached to opposing ends of the network 210 or frame 150. Embodiments of the housing mounting bracket 170 can be configured to be reversibly connected (e.g., by snap-fitting, bolting, clamping or other conventional means) to fixtures 175 of the HVAC housing 107. A reversible connection to the housing 107 can facilitate the servicing and replacement of components of the unit 100, e.g., for cleaning the network 210, the heat exchanger 105 or drain pan 106, or, for replacing the light source 120.

Figure 5:
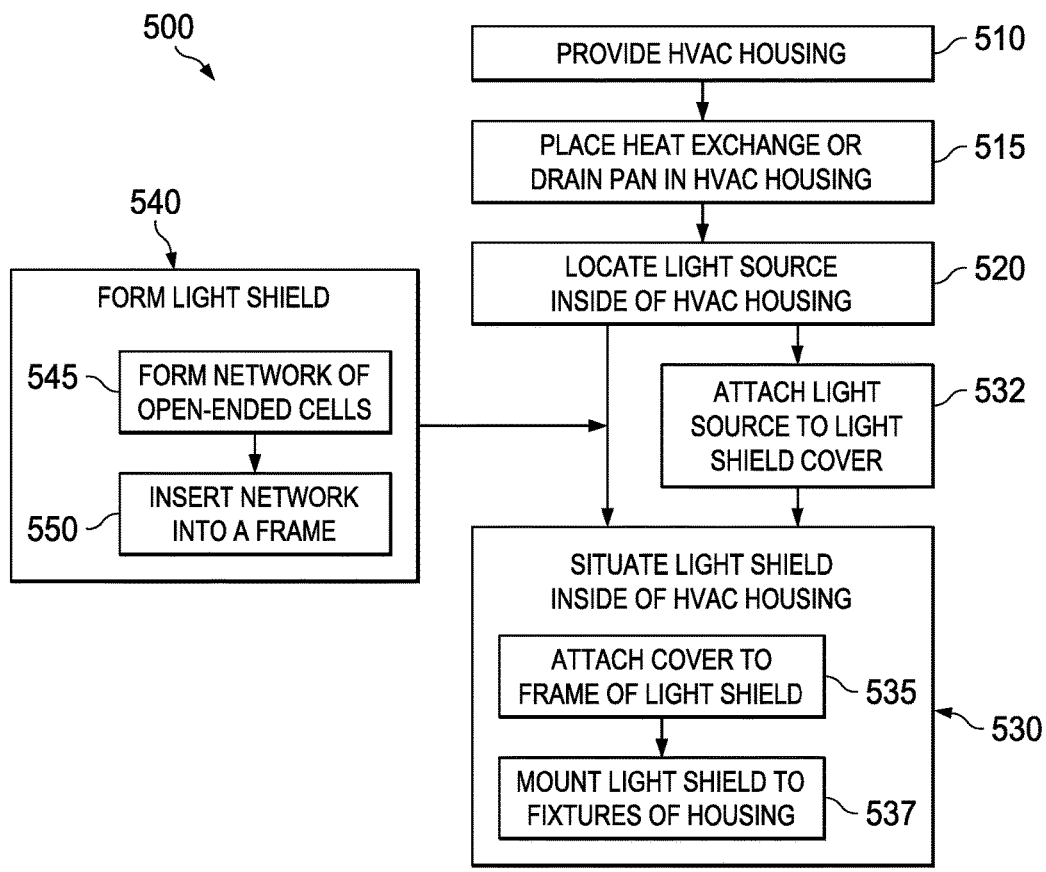
FIG. 5 presents a flow diagram of an example method of manufacturing a HVAC unit of the disclosure, such as the unit and its component part depicted in FIGS. 1-4.

Another embodiment of the present disclosure is a method of manufacturing a HVAC unit. FIG. 5 presents a flow diagram of an example method 500 of manufacturing a HVAC unit of the disclosure, such as the HVAC unit 100 with its component parts, as depicted in FIGS. 1-4, which are referred to throughout.

The method 500 comprises a step 510 of providing a HVAC housing 107 having one or more access openings 110 and ultraviolet light-sensitive components 117, 118. One skilled in the art would be familiar with the manufacture and assembly of housings 107 suitable for HVAC applications. The method 500 also comprises a step 515 of placing a heat exchanger 105 or a drain 106 (or both) inside of the HVAC housing such that the heat exchanger 105 is located between paths for conditioned air and return airflow. Those skilled in the art would be familiar with various embodiments of heat exchangers 105 or drain pans 106 that can be used in HVAC applications, and, with procedures to optimally locate the heat exchange 105 in the housing 107 so as to be in the airflow's path.

The method 500 also comprises a step 520 of locating a light source 120 inside of the HVAC housing 107 such that UV light 124 emitted from the light source 120 can reach the heat exchanger 105 or drain pan 106. In some cases, the light source 120 is located inside of the housing in step 520 by being incorporated into a light shield 122 which is then situated inside of the housing 107 as further discussed below. In other cases, however, the light source 120 can be separately attached to the housing 107.

The method further comprises a step 530 of situating at least a portion of the light shield 122 between the heat exchanger 105 or drain pan 106 and the light source 120. As discussed above in the context of FIGS. 1-4, the light shield 122 includes a network 210 of open-ended cells 220 and each cell 220 has UV light reflective walls 230. The light shield 122 is oriented to direct UV light 124 from the light source 120 through the open-ended cells 220 towards the heat exchanger 105 or drain pan 106 and away from the one or more access openings 110 and ultraviolet light-sensitive components 117, 118.

In some cases, the light source 120 and light shield 122 can be separately located (step 520) and situated (step 530) inside of the housing 107. In some cases, situating the light shield 122 in step 530 includes attaching the light source 120 to the cover 155 of the light shield 122 in step 532, attaching the cover 155 to the frame 150 of the light shield 122 in step 535 and then mounting the light shield 122 to fixtures 175 in the housing in step 537. In some cases, situating the light shield 122 in step 530 includes reversible connecting mounting brackets 160 of the light shield 122 to the fixtures 175 in step 537. In some cases, mounting the light shield to the fixtures 175 in step 537 is such that it provides the light shield 122 with the desired orientation, with no further adjustments to its position needed. In other cases, one or both the mounting brackets 170 or fixtures 175 are adjustable so as to facilitate more precise situating of the light shield in accordance with step 530.

Some embodiments, of the method 500 further includes forming the light shield 122 in step 540. Forming the light shield in step 540 can include a step 545 of forming the network 210 of open-ended cells 220. For instance, forming the network 210 (step 545) can include adhering a plurality of material layers (e.g., aluminum or steel layers) together by laying down glue in line segments on successive material layers before pressing the material layers together. The line segments of glue can be uniformly spaced apart various grid patterns in accordance to the desired sizes of open areas 350, 352 and geometric patterns of the cells 220. After the glue has dried the layers are pulled apart to form the network 210 of open ended cells 220.

Forming the light shield 122 in step 540 can also include a step 550 of inserting the network 210 into a frame 150 that is configured to shape the network 210 into a target shape. For instance, in some cases, the frame 150 is configured to shape the network into a cylindrical hemi-annular shape (see e.g., frame 150 and network 210 depicted FIG. 2). For instance, in some cases, the frame 150 is configured to shape the network 210 into a planar rectangular shape (see e.g., frame 150 and network 210 depicted in FIG. 4).

Those skilled in the art to which this application relates will appreciate that other and further additions, deletions, substitutions and modifications may be made to the described embodiments.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A housing for one or more components of a heating, ventilating and air conditioning (HVAC) unit, comprising:
   one or more ultraviolet light-sensitive components;
   a plurality of light sources located inside of said housing; and
   a plurality of light shields at least partially located between the one or more components and said plurality of light sources, and at least partially located between the one or more ultraviolet light-sensitive components and said plurality of light sources, the plurality of light shields comprising a network of open-ended cells, each cell having ultraviolet light reflective walls, the plurality of light shields configured to have a fixed orientation relative to said plurality of light sources, wherein the fixed orientation causes said plurality of light shields to direct an ultraviolet light from said plurality of light sources through said open-ended cells towards the one or more components and away from the one or more ultraviolet light-sensitive components.

2. The unit of claim 1, wherein the plurality of light shields comprise a mounting bracket configured to connect to a plurality of fixtures located proximate the one or more components.

3. The unit of claim 2, wherein the one or more components are located on one side of the housing and a distal side of the housing comprises a plurality of blowers.

4. The unit of claim 2, wherein the plurality of light shields extends from a drain pan to the plurality of fixtures.

5. The unit of claim 1, further comprising a plurality of access openings and plurality of access panels configured to cover the access openings and to be removed during operation to give access to the interior of the housing.

6. The unit of claim 3, wherein said network of open-ended cells form a substantially planar rectangular shape and said plurality of blowers comprises a first plurality of ultraviolet light sensitive components and the plurality of light shields is configured to direct light away from said first plurality of ultraviolet light sensitive components.

7. The unit of claim 1, wherein said light shield further includes a frame configured to maintain said network's shape.

8. The unit of claim 1, wherein said light shield includes a cover configured to hold said light source a fixed distance away from said network.

9. The unit of claim 1, wherein said light shield includes a cover that has an interior surface that is UV light reflective.

10. The unit of claim 1, wherein said light shield includes a housing mounting bracket configured to connect said light shield to said housing so as to have said orientation.

11. The unit of claim 1, wherein said light source includes one or more cylindrically-shaped light bulbs, each said bulbs having a long axis that is substantially centrally aligned with and parallel to the one or more components.

12. The unit of claim 11, wherein said network has a cylindrical hemi-annular shape that at least partially circumscribes said long axis of said bulb, said long axis being located substantially at a radial center of said hemi-annulus.

13. The unit of claim 1, wherein opposing surfaces of said network and said light source are separated by a distance that ranges from about 1 to 10 cm.

14. The unit of claim 1, wherein a surface of said network is separated from said one or more components or drain pan by a distance that ranges from about 10 to 30 cm.

15. The unit of claim 1, wherein said orientation of said light shield in said housing is such that said ultraviolet light projects out of said network over an angle that ranges from about 45 to 180 degrees.

16. A method of manufacturing a housing for a heating, ventilating and air conditioning (HVAC) unit, comprising:
   providing a housing having one or more access openings and one or more ultraviolet light-سensitive components;
   placing one or more components in said housing such that the one or more components are located between paths for conditioned air and return airflow;
   locating a light source inside of said housing such that ultraviolet light emitted from said light source can reach the one or more components;
   situating a light shield in the housing and at least partially between the one or more components and said light source, and at least partially between the one or more ultraviolet light-sensitive components and said light source, wherein the light shield comprises a network of open-ended cells, each cell having ultraviolet light reflective walls, and
   situating said light shield to have a fixed orientation relative to said light source, wherein the fixed orientation causes said light shield to direct an ultraviolet light from said light source through said open-ended cells towards the one or more components and away from the one or more ultraviolet light-sensitive components.

17. The method of claim 16, wherein situating said light shield includes connecting mounting brackets of said light shield to fixtures of said housing such that said light shield has said orientation, wherein said mounting brackets are reversibly connected to said fixtures.

18. The method of claim 16, further including forming said light shield including: forming said network of open-ended cells; and inserting said network into a frame configured to shape said network into a target shape.

19. The method of claim 18, wherein said frame is configured to form said network into a cylindrical hemi-annular shape.

20. The method of claim 16, wherein locating said light source inside of said housing includes attaching said light source to a cover of said light shield.

* * * * *